United States Patent
Jakob et al.

(10) Patent No.: US 6,544,272 B1
(45) Date of Patent: Apr. 8, 2003

(54) TISSUE HOLDER

(75) Inventors: Roland P. Jakob, Môtier (CH);
Werner Müller, Wiesendangen (CH);
Heribert Frei, Winterthur (CH)

(73) Assignee: Sulzer Orthopedics Ltd., Baar (CH)

( * ) Notice: Subject to any disclaimer, the term of this patent is extended or adjusted under 35 U.S.C. 154(b) by 236 days.

(21) Appl. No.: 09/654,145

(22) Filed: Sep. 1, 2000

(30) Foreign Application Priority Data

Sep. 29, 1999 (EP) .............................................. 99810880

(51) Int. Cl.⁷ .................................................. A61F 17/08
(52) U.S. Cl. ........................................ 606/151; 606/213
(58) Field of Search ............................... 606/60, 65, 66, 606/72, 77, 86, 144, 151, 152, 153, 61, 73, 219; 623/1.22, 13.11, 13.12, 13.14, 13.17, 13.18, 14.12

(56) References Cited

U.S. PATENT DOCUMENTS

| | | | |
|---|---|---|---|
| 5,171,278 A | * 12/1992 | Pisharodi | 128/898 |
| 5,190,545 A | * 3/1993 | Corsi et al. | 606/60 |
| 5,474,557 A | 12/1995 | Mai | |
| 5,500,013 A | * 3/1996 | Buscemi et al. | 604/104 |
| 5,540,701 A | * 7/1996 | Sharkey et al. | 606/153 |
| 5,582,619 A | * 12/1996 | Ken | 606/108 |
| 5,810,851 A | 9/1998 | Yoon | |
| 5,810,882 A | * 9/1998 | Bolduc et al. | 606/151 |
| 5,855,599 A | * 1/1999 | Wan | 128/830 |
| 5,957,940 A | 9/1999 | Tanner | |
| 6,171,338 B1 | * 1/2001 | Talja et al. | 623/1.22 |
| 6,231,583 B1 | * 5/2001 | Lee | 606/151 |
| 2002/0010481 A1 | * 1/2002 | Jayaraman | 606/151 |
| 2002/0055742 A1 | * 5/2002 | Lieberman | 606/73 |

FOREIGN PATENT DOCUMENTS

| | | |
|---|---|---|
| EP | 0913123 A1 | 5/1999 |
| FR | 2719993 | 11/1995 |
| WO | WO 99/01071 | 1/1999 |

* cited by examiner

*Primary Examiner*—David O. Reip
*Assistant Examiner*—D. Jacob Davis
(74) *Attorney, Agent, or Firm*—Townsend and Townsend and Crew LLP

(57) ABSTRACT

A tissue holder (1, 1a) has a first connector (2, 2a) which can be connected to a tissue part and a second connector (3, 3a) which can be connected to a further tissue part. The tissue holder further holds the two connectors (2, 2a; 3, 3a) and thus the tissue parts relative to one another. The first and second connectors (2, 2a; 3, 3a) each have at least one curved spike (21, 22, 21a, 22a; 31, 32, 31a, 32a) which extends around the longitudinal axis of the tissue holder (1, 1a).

10 Claims, 2 Drawing Sheets

TISSUE HOLDER

Figure 1:
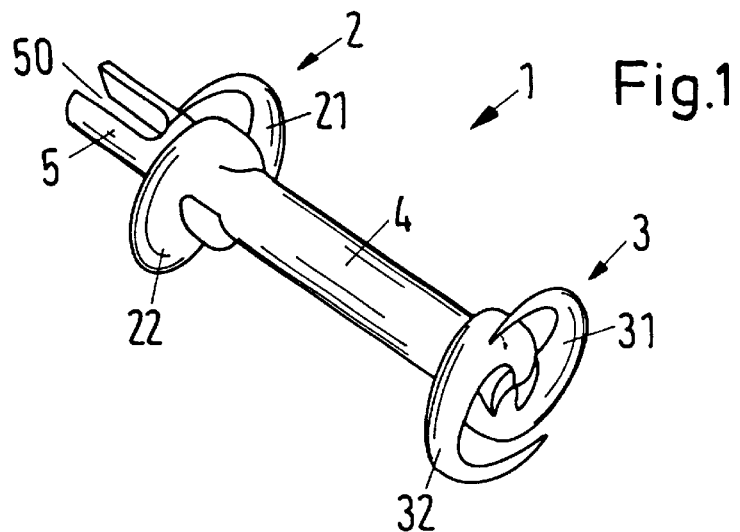

The invention relates to a tissue holder in accordance with the preamble of the independent patent claim.

In tissue lesions one would wish to achieve as good and rapid a healing process as possible in the normal case. This also holds in particular for lesions of the meniscus of the knee, especially for small tears in the meniscus. Such meniscus lesions do not heal spontaneously in the adult human, but rather the tissue parts must be pressed against one another and fixed for this purpose. Only a sufficient pressing together of the tissue parts against one another permits a healing process. The goal after a healing is as smooth a surface of the meniscus after the operation without scratches etc. as possible, because of course the femur condyles slide on this meniscus surface and the articulation surfaces of the condyles are cartilaginous and are therefore very sensitive to scratches in the meniscus surface.

In order to effect a sufficient pressing together of the tissue parts against one another and to hold the tissue parts in this position, different treatment methods have been established. One such treatment technique is the fixing of the tissue parts by sutures, with the most diverse of suturing techniques being used. The suturing of a meniscus tear and an instrument which is suitable for this is for example described in WO-A-98/31288. This kind of fixing (suturing) of the tissue parts is admittedly reliable, but is relatively complicated in regard to the operating technique, especially when the intrusion is carried out arthroscopically (accessibility), which is increasingly the case in such cases and probably already represents the rule.

A further treatment technique is the fixing of the tissue parts through the introduction of an implant. Used in this as implants are for example pins with barbs at the pin body (first securing means) and with a projection (second securing means) at the blunt end of the pin body, such as for example is described in WO-A-97/18761. The barbs become hooked in the tissue part on the other side of the tear after the introduction, draw this tissue part in the direction towards the projection at the blunt end of the pin in the part of the tear on this side and hold the two tissue parts in this position, so that the tear can heal. Other implants which are used in the fixing of the tissue parts are for example screws having two sections which are in each case provided with a thread. The two threads (first and second securing means) have however a different pitch (see e.g. U.S. Pat. No. 5,569,252). Through this different pitch of the threads, when the one thread engages on the other side of the tear and the other thread engages on this side of the tear in the meniscus, the two tissue parts are drawn together and held in this position so that the tear can heal.

In these kinds of the fixing of the tissue parts with the help of implants the implant (the pin with the barbs or the screw respectively) is introduced in each case centrally, i.e. in the middle, in relation to the thickness of the meniscus. In any case it is important that absolutely no part of the implant projects into the meniscus surface, since the femur condyles must of course slide on this surface. These kinds of fixing (by means of implants) are simpler in regard to the operating technique than the suturing techniques. With increasing age of the patient, however, it becomes more difficult to use this type of fixing because the inner part ("core") of the meniscus becomes increasingly mucoid, that is, soft, so that the implants can only be very poorly fixed in the interior ("core") of the meniscus. Recourse is then increasingly had to the already described suturing techniques, which are however comparatively more complicated in regard to the operating technique, because the central anchoring of the implant (in the "core" of the meniscus) no longer comes under consideration.

The object of the invention is thus to propose a tissue holder (implant) which can be simply secured at the tissue parts and which holds the tissue parts in a desired position relative to one another. In particular this tissue holder should be suitable for the treatment of tears in the meniscus and indeed also for patients in which the inner part ("core") of the meniscus is already soft, so that recourse would otherwise be had to suturing techniques.

This object is satisfied in accordance with the invention by a tissue holder such as is characterized by the features of the independent patent claim. Particularly advantageous embodiments of the tissue holder in accordance with the invention result from the subordinate patent claims.

In particular the first and second securing means of the tissue holder (the securing means on this side and the other side of the tear) comprise at least one curved spine which extends around the longitudinal axis of the tissue holder. Thus even if the tissue holder is introduced centrally, that is, into the soft "core" of the meniscus, the connecting with the two tissue parts takes place with the help of the curved spike, which extends around the longitudinal axis of the tissue holder, that is, not in the "core" of the meniscus, but rather in a region beneath the surface of the meniscus, where the meniscus still has sufficient strength in order to achieve a sufficiently good fixing of the tissue holder. The tissue holder can thus—when all is considered—quite well be introduced into the possibly soft "core" of the meniscus, since the connection to the tissue lies just in a range (beneath the surface of the meniscus) where the tissue has a sufficient strength in order to achieve a good fixing of the tissue holder.

In an advantageous exemplary embodiment, the means which hold the spikes and thus the tissue parts relative to one another comprise a connecting web which extends in the direction of the longitudinal axis of the tissue holder. In this the spikes extend around this connecting web. In regard to the constructional design and the handling this is a relatively simple and quite functional embodiment variant of the tissue holder.

In an advantageous further development the axial distance between the spike or the spikes respectively of the first securing means and the spike or the spikes respectively of the second securing means increases in the direction towards the free end of the spikes, that is, this distance decreases in the direction towards the connecting web starting from the free ends of the spikes. This causes the tissue parts to be able to be drawn together in the rotating in of the tissue holder (as is desirable in the treatment of a tear in the meniscus), and the tissue holder thus to act as a clamp.

In an advantageous further development the spikes extend helically around the longitudinal axis of the tissue holder or around the connecting web respectively. Through this helical shape it can be achieved that during the rotating in of the tissue holder the two tissue parts are drawn together and the tissue holder acts as a clamp. In principle it is however also possible (namely, when the distance between the spike or the spikes respectively of the first securing means and the spike or the spikes respectively of the second securing means decreases in the direction towards the ends of the spikes) to draw the tissue parts apart, in so far as this is desirable. In the above named treatment of a tear in the meniscus this however does not hold.

In a further development of this tissue holder the axial thickness of a spike decreases in the direction towards the free end of the spike. Through this the helical shape can be achieved and it can be effected that during the rotating in of the tissue holder the two tissue parts are drawn together and the tissue holder acts as a clamp. Depending on the manner in which the axial thickness decreases, it can also be achieved that during the rotating in of the tissue holder the tissue parts are drawn apart, in so far as this is desirable.

In another further development the spikes are designed substantially cylindrically, but they nevertheless extend helically however. At the free end the spikes can naturally taper in order to facilitate the penetration into the respective tissue part. With this further development as well, either the function of a clamp can be effected or the tissue parts can be drawn apart, depending on how the helix extends.

In a further exemplary embodiment of the tissue holder the first and the second securing means comprise in each case two spikes, with the spikes of the respective securing means starting from the connecting web at oppositely lying positions and then extending in the same direction around the connecting web. This has the advantage that in the introduction of the tissue holder the tissue holder need not be rotated very far even in unfavorable cases until a spike pierces in into the respective tissue part and is thus connected to the respective tissue part.

In a further advantageous exemplary embodiment an extension piece for a tool, by means of which a connection of the tissue holder to the tissue parts can be effected, is provided at the tissue holder. This extension piece can for example have a reception slit for a rotation tool (in the manner of a screwdriver) or else be designed differently in order to enable the movement of the tissue holder by a tool.

Finally, it is advantageous when the tissue holder is manufactured of a bio-absorbable material, in particular of polylactides. Through this on the one hand the desired fixing and healing takes place, and on the other hand the tissue holder need not be removed once again through an operative intervention.

Figure 2:
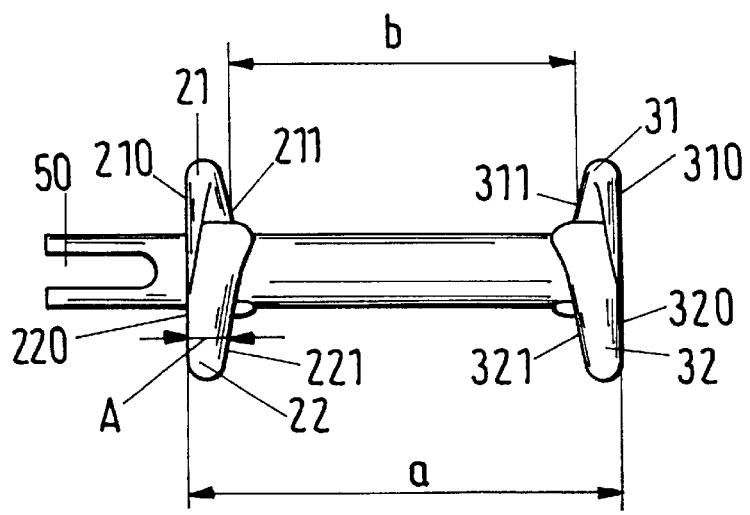
Figure 3:
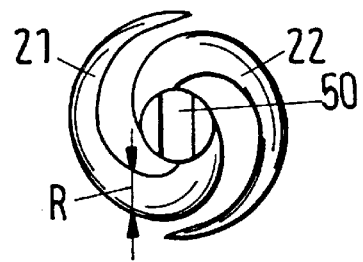
Figure 4:
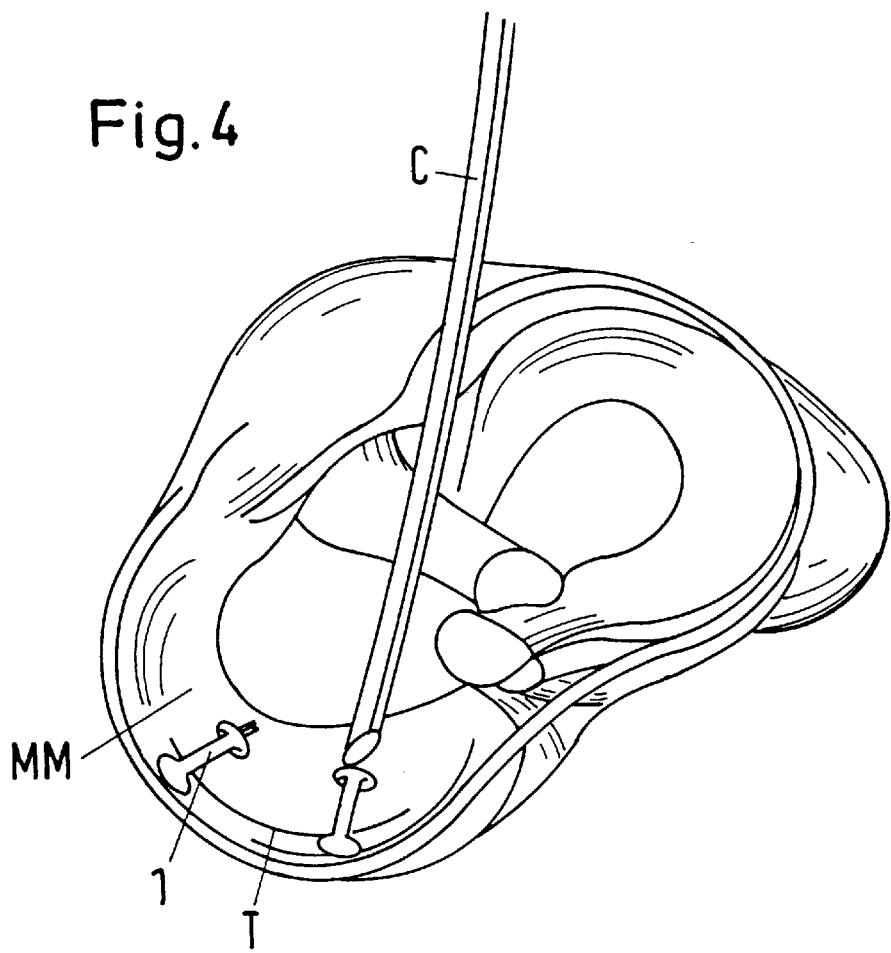
Figure 5:
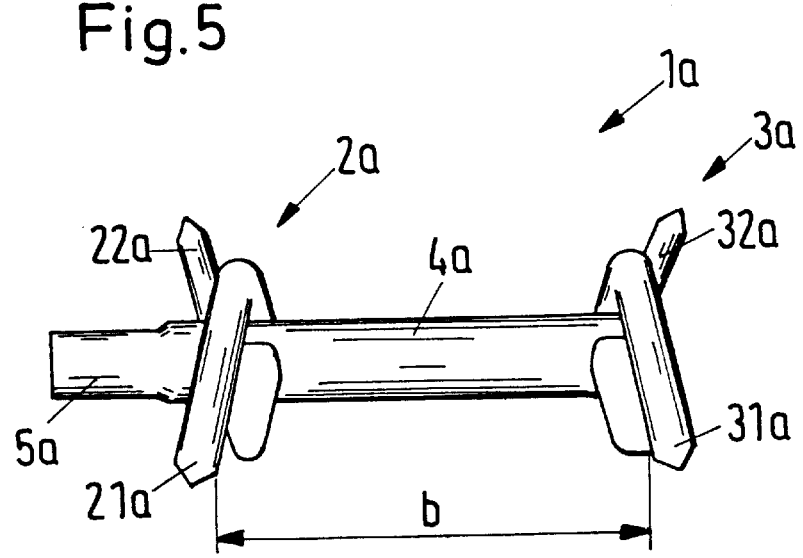

The invention will be explained in more detail in the following with reference to the drawings. Shown in these in schematic illustration and/or partly in section are:

FIG. 1 a perspective view of an exemplary embodiment of a tissue holder in accordance with the invention, FIG. 2 a side view of the tissue holder of FIG. 1, FIG. 3 a front view of the tissue holder in accordance with FIG. 1 from the direction of the extension piece, FIG. 4 a schematic illustration for explaining the introduction of the tissue holder in the treatment of a tear in the inner meniscus (meniscus medialis) and FIG. 5 a further exemplary embodiment of a tissue holder in accordance with the invention in a side view.

In FIG. 1 one recognizes an exemplary embodiment of a tissue holder 1 in accordance with the invention. The tissue holder 1 in accordance with the invention has first securing means 2 in the form of two spikes 21 and 22 as well as second securing means 3 in the form of two spikes 31 and 32 which can be connected to the tissue parts on this side and on the other side of a tear in the meniscus (see FIG. 4). A connecting web 4 extends between the first securing means 2 and the second securing means 3. Furthermore, one recognizes in FIG. 1 that the tissue holder also has an extension piece 5 for a tool (not illustrated), with the help of which the tissue holder 1 can be connected to the tissue parts (e.g. to the meniscus parts on this side and on the other side of the tear, see FIG. 4). The extension piece 5 can for example be provided with a slit 50, as shown in FIG. 1 and FIG. 2, into which a rotation tool can engage in accordance with the principle of the screwdriver; but other means can however also be provided by means of which a movement of the tissue holder 1 can be effected.

From FIG. 1 and FIG. 2 one recognizes that the spikes 21 and 22 of the first securing means 2 and the spikes 31 and 32 of the second securing means 3 respectively are curved and extend in each case around the connecting web 4 starting from the connecting web 4. In FIG. 3 one recognizes that the spikes 21 and 22 (corresponding remarks hold for the spikes 31 and 32) extend helically around the connecting web 4. In principle it would be sufficient if the first securing means 2 and the second securing means 3 in each case were to have only one spike each; the illustrated exemplary embodiment with two spikes each which start from the connecting web 4 at oppositely lying positions, and are thus displaced by about 180° over the periphery of the connecting web 4, is however advantageous in so far as the tissue holder 1 need not be rotated about a large angle when being introduced, but rather pierces into the respective tissue part rapidly. In this the two spikes 21 and 22 as well as 31 and 32 extend in each case in the same direction around the connecting web 4 and are shaped helically.

Because the spikes 21 and 22 as well as 31 and 32 extend around the connecting web 4 the tissue holder 1—considered as a whole—can be introduced into the "core" of the meniscus, even if the latter is already soft and would no longer enable a good anchoring for a tissue holder of this kind, since of course the spikes engage into the meniscus in a region beneath the surface of the meniscus, that is, in a region where the meniscus has a sufficient strength in order to ensure a good anchoring of the tissue holder. At the same time the surface of the meniscus remains unimpaired by the spike, which is important for an unobjectionable cooperation of the articulation surface of the respective femur condyle with the meniscus.

In FIG. 3 one easily recognizes that the radial thickness R of the spikes 21 and 22 (corresponding remarks hold for the spikes 31 and 32) decreases in the direction towards the free end of the respective spike starting from the connecting web 4. This provides a foundation on the one hand for a stable securing of the spikes at the connecting web 4, and on the other hand the spikes must be sharpened to a certain extent at the free end in order that they can penetrate into the tissue parts (here: meniscus parts). In this the spike can project slightly outwardly beyond the tangential direction at the free end—as is shown in FIG. 3, so that when rotated in, the spike pierces into the relevant tissue part in any case and can not, say, slip through under the tissue part.

The axial thickness A of the spikes also decreases in the direction towards the free end of the respective spike starting from the connecting web 4, which can easily be recognized in FIG. 2. This holds in the present exemplary embodiment both for the spikes 21 and 22 of the first securing means 2 as well as for the spikes 31 and 32 of the second securing means 3. In this the respective surfaces of the spikes 21 and 22 of the first securing means 2 which point outwardly in the axial direction and the surfaces of the spikes 31 and 32 of the second securing means 3 which point outwardly extend in a plane which is perpendicular to the axial direction, that is, perpendicular to the longitudinal axis of the connecting web 4. The distance a between the outwardly pointing surfaces 210 and 220 respectively of the spikes 21 and 22 of the first securing means 2 and the correspondingly outwardly pointing surfaces 310 and 330 respectively of the spikes 31 and 32 of the second securing means 3 is thus constant. The distance b between the inwardly pointing surfaces 211 and 221 respectively of the spikes 21 and 22 of the first securing means 2 and the correspondingly inwardly pointing surfaces 311 and 321 respectively of the spikes 31 and 32 of the second securing means 3 decreases in the direction towards the connecting web 4 however—when considered to start from the free end of the spikes. This leads to the helical shape and, when the tissue holder 1 is being introduced, causes the two tissue parts to be drawn together when the tissue holder 1 is rotated in and thus to achieve the action of a clamp. In principle it would be sufficient for achieving this clamp action if only the first securing means 2 or only the second securing means 3 had spikes, the inwardly pointing surfaces of which are designed as described above. Since this is however the case in both securing means, the clamp action is further increased.

It is easy to see that if it is desired to draw tissue parts apart, the spikes can be formed in such a manner that the distance between the inwardly pointing surfaces of the spikes is held constant and the distance between the outwardly pointing surfaces increases (when viewed from the web to the free end) in order to draw apart the tissue parts and to hold them then in this position. In this way a spreading action can be achieved.

It is particularly advantageous when the tissue holder 1 is manufactured of bio-absorbable material, in particular of polylactides. Then, namely, the tear can on the one hand be held together, so that the fixing and the healing can take place; on the other hand no further operative intervention need be carried out in order to remove the tissue holder 1 again later.

It is schematically indicated in FIG. 4 how a tissue holder can be introduced in the case of a tear T in the inner meniscus MM (meniscus medialis). A tissue holder 1 has already been introduced in the region of the front end of the tear T. It is just being introduced in the region of the rear end. For this a cannula C is first pierced completely through the tear T until it has just penetrated into the other meniscus part. The tissue holder 1 is then pushed through the inner space of this cannula C with a screwdriver (not illustrated) which engages into the slit 50 of the extension piece 5 (see FIG. 1 and FIG. 2) up to the front end of the cannula C. The screwdriver can have a bore at its distal end which surrounds the actual blade of the screwdriver. This bore receives the extension piece 5 of the tissue holder. The blade of the screwdriver, which is surrounded by the bore, can then engage into the slit 50 of the extension piece 5 without the blade being able to slide radially out of the slit 50, since it is captured in the bore which surrounds the blade. The friction between the tissue holder 1 and the screwdriver is sufficient to prevent an axial sliding out of the tissue holder 1 out of the bore of the screwdriver.

If now the cannula C has just penetrated through the tear T and into the other meniscus part, then the screwdriver is pushed forward with the tissue holder 1 into the cannula C up to the distal end of the cannula. Then the cannula C is drawn back to a slight extent. Afterwards the tissue holder 1 is rotated with the help of the screwdriver. The spikes 21 and 22 respectively and 31 and 32 respectively then penetrate into the tissue part which is arranged on this side of the tear T and on the other side of the tear T; and through a further rotating (e.g. ¼ of a rotation at the maximum) of the tissue holder the tissue parts are drawn together and the tear T is closed in this manner.

Prior to the introduction of the cannula C the tissue parts can already have been pretreated at both sides of the tear T in such a manner that the edges of the tissue parts have already been machined with the help of an arthroscopic file or a mechanical shaver respectively in order to stimulate the perimeniscal synovium to a healing response. Then the tissue parts can be held together until finally with the help of the cannula C the tissue holder 1 is introduced and subsequently fixed, so that the tear T is finally drawn together—with the tissue holder 1 having been introduced—in the manner of a clamp, so that the tear T can heal.

A further exemplary embodiment of a tissue holder 1a in accordance with the invention is shown in FIG. 5. This exemplary embodiment likewise has, like the exemplary embodiment in accordance with FIG. 1, first and second securing means 2a and 3a which in turn have two spikes 21a and 22a and, respectively, 31a and 32a, which extend around the connecting web 4a. In contrast to the above described exemplary embodiment of the tissue holder, however, the spikes here are substantially (i.e. with the exception of the extension at the connecting web, which is made somewhat thicker, as well as the free end, which runs a bit to a point) designed in cylindrical shape. However they extend nevertheless in the shape of a helix, and indeed in the direction away from one another, when the spikes 21a, 22a, 31a, 32a of the first and second securing means 2a and 3a are considered relative to one another and are followed in the direction towards their free end. Through this the distance b between the inwardly pointing surfaces of the spikes 21a, 31a and 22a, 32a respectively becomes smaller when the course of the spikes is followed in the direction towards the connecting web 4a as considered from the free end. In this way the clamp action which was described above with reference to the other exemplary embodiment can likewise be achieved in the rotating in. The rotating in of the tissue holder 1a can take place analogously as described above; for this purpose an extension piece 5a is likewise provided in the exemplary embodiment described. Through a reversal of the helical course of the spikes 21a, 22a and 31a, 32a respectively in the direction towards the spikes of the other securing means (again considered in the direction towards the free end of the respective spike), it would be possible, if desired, to achieve a spreading action, that is, a drawing apart of the tissue parts.

What is claimed is:

1. Tissue holder, comprising first securing means which can be connected to a tissue part and second securing means which can be connected to a further tissue part, said tissue holder further comprising means which hold the first and second securing means and thus the tissue parts relative to one another, the first and second securing means each including at least one curved spike which extends around a longitudinal axis of the tissue holder, and means holding the spikes and thus the tissue parts relative to each other comprising a connecting web extending in the direction of the longitudinal axis of the tissue holder, the spikes extending around the connecting web.

2. Tissue holder in accordance with claim 1 wherein an axial distance between the spike or the spikes respectively of the first securing means and the spike or the spikes respectively of the second securing means increases in a direction towards free ends of the spikes and decreases in a direction towards the connecting web starting from the free ends of the spikes.

3. Tissue holder in accordance with claim 1 wherein the spikes extend helically around the longitudinal axis of the tissue holder or around the connecting web respectively.

4. Tissue holder in accordance with claim 3 wherein an axial thickness of a spike decreases in a direction towards the free end of the spike.

5. Tissue holder in accordance with claim 3 wherein the spikes are substantially cylindrical.

6. Tissue holder in accordance with claim 1 wherein the first and second securing means each comprise first and second spikes, the spikes of the respective securing means starting from the connecting web at oppositely lying positions and extending in the same direction around the connecting web.

7. Tissue holder in accordance with claim 1 including an extension piece for a tool which effects a connection of the tissue holder to the tissue parts.

8. Tissue holder in accordance with claim 1 comprising a bio-absorbable material.

9. Tissue holder according to claim 8 wherein the bioabsorbable material comprises polylactides.

10. Tissue holder, comprising first securing means which can be connected to a tissue part and second securing means which can be connected to a further tissue part, said tissue holder further comprising a connecting web and means which hold the first and second securing means and thus the tissue parts relative to one another, the first and second securing means each including two curved spikes, the spikes of the respective securing means starting from the connecting web at oppositely lying positions and then extending in the same direction around the connecting web.

* * * * *